US006176236B1

(12) United States Patent
Tebbe

(10) Patent No.: US 6,176,236 B1
(45) Date of Patent: Jan. 23, 2001

(54) OXYGENATING DEVICE

(76) Inventor: Gerold Tebbe, 22. Av., Princesse Grace MC-9800 (MC)

(*) Notice: Under 35 U.S.C. 154(b), the term of this patent shall be extended for 0 days.

(21) Appl. No.: 08/687,575

(22) PCT Filed: Dec. 8, 1995

(86) PCT No.: PCT/EP95/04834

§ 371 Date: Sep. 20, 1996

§ 102(e) Date: Sep. 20, 1996

(87) PCT Pub. No.: WO96/18369

PCT Pub. Date: Jun. 20, 1996

(30) Foreign Application Priority Data

Dec. 11, 1994 (DE) ........................................ 44 44 135

(51) Int. Cl.[7] ........................................ A61M 15/00
(52) U.S. Cl. ........................ 128/202.13; 128/202.18
(58) Field of Search .................. 128/202.13, 202.18, 128/202.12, 205.26

(56) References Cited

U.S. PATENT DOCUMENTS 2,917,046 * 12/1959 Fairbanks .................... 128/202.18
3,859,993 * 1/1975 Bitner .................... 128/205.26
3,898,427 * 8/1975 Levin et al. .................... 128/205.26
4,377,161 * 3/1983 Whitt .................... 128/205.26
4,523,588 * 6/1985 Dolsky .................... 128/202.18
4,739,753 * 4/1988 Brehm .................... 128/205.26
5,038,431 * 8/1991 Burgin et al. .................... 128/202.18
5,188,099 * 2/1993 Todeschini et al. .................... 128/202.12
5,305,483 * 4/1994 Watkins .................... 128/202.18
5,317,767 * 6/1994 Hargest et al. .................... 128/202.18

FOREIGN PATENT DOCUMENTS

0491145 A2 * 6/1992 (EP) .

* cited by examiner

*Primary Examiner*—Aaron J. Lewis

(57) ABSTRACT

For oxygen enrichment of the blood during sleep the invention proposes that oxygen-enriched air be fed into the space between the cover and the top side of the mattress of a bed. This is done in part through the interior of the mattress with an air-permeable cover layer, in part through a soft interposed mat laid over the sleeper.

26 Claims, 4 Drawing Sheets

OXYGENATING DEVICE

The invention concerns a treatment device for supplying a person with additional oxygen in accordance with the preamble of claim 1.

As a source for the treatment gas, known oxygenating devices of this type comprise a pressure cylinder filled with oxygen which is connected via a reducing valve to a hose, the free end of which has a face mask attached to it. In this way a specific and loss-free supply of oxygen to the user can be guaranteed. For long-term therapy in particular, however, this method is not very acceptable because the wearing of a face mask in treatment sessions is unpleasant and the treatment takes up a lot of time which cannot be used for other purposes.

It has now been recognised that an oxygen enrichment of blood in human beings can also be brought about by cutaneous respiration. It has further been recognised that between the top side of the mattress of a bed and the cover lying over a sleeping person there is a space which is quite well sealed from the environment which provides good flow contact with the skin of the sleeper through the thin night clothes. By virtue of the device according to the invention, this space which encompasses a large part of the surface of the skin is supplied with oxygen or with oxygen enriched air through an appropriate conducting device.

The supply of additional oxygen into the circulation through cutaneous respiration is, it is true, less intensive than the supply through inhaled air, but this can largely be compensated for by a considerably longer treatment period. In addition, the supply of extra oxygen in this way in no way involves the user in any unpleasantness, nor does it involve any extra time; it is done during sleep. The additional oxygen emerging from the space lying between the cover and the surface of the mattress also provides oxygen enrichment in the immediate environment around the sleeper so that an additional oxygen enrichment of the blood is obtained by the sleeper breathing in any oxygen in the space which has not been consumed.

Further advantageous embodiments of the invention are given in the subclaims.

The further embodiment of the invention according to claim 2 is of advantage in respect of undisturbed sleep comfort and the evenly distributed supply of the treatment gas into the space.

The further embodiment of the invention according to claim 3 also serves to provide an even distribution of the treatment gas without any impairment in sleep comfort.

According to claims 4 to 6 an open pore internal structure of the interposed mat can be achieved simply and in a user-friendly manner.

If, in order to feed the treatment gas into the space, as interposed mat is used which lies over the sleeping person, then the oxygen emerging from this mat first of all reaches those parts of the skin which are uppermost. In order to supply the lowermost parts of the skin, a similar interposed mat can be used in principle; since, however, pressure is applied on this by the weight of the sleeping person, its porous internal structure must be somewhat harder in design, although as a rule no loss in comfort is perceived since the surface of a mattress is generally quite a lot harder than the cover lying over the sleeping person.

In the case of a device according to claim 7, use is made of the fact that in the mattress itself you already have a structure which allows a certain rate of air flow and which also supports the body evenly and comfortably and which, with a slight modification, can also take over the role of supplying oxygen to the lower parts of skin of a sleeping person. With a device according to claim 7 the area of the bed underneath the sleeping person essentially has the same construction as a conventional bed.

The use of an interior sprung mattress as an interposed structure as is indicated in claim 8, is advantageous with respect to achieving optimum permeability and uniform supply of oxygen.

In the construction of the mattress forming the interposed structure according to claim 9, the release of oxygen into the environment of the bed is kept small.

The further embodiment of the invention according to claim 10 is of advantage with respect to the fact that a standard sheet is laid on the mattress.

Mattresses normally have two choices of surfaces on which to lie for summer or winter use. In a further embodiment of the invention according to claim 11, when a double-sided mattress of this type is used, whichever surface of the mattress is bottom-most is sealed so that it is impermeable to the circulating medium, so that no oxygen is able to escape through it.

With a device according to claim 12 the circulating medium link between the interior of the mattress and the oxygen supply line is achieved automatically when the mattress is laid on the base.

With the further embodiment of the invention according to claim 13 a double-sided mattress guarantees that any time that the supply line connection is not needed it is automatically sealed if it is not in use and is compulsorily opened whenever it is connected to the supply line.

A device of the type described in claim 14 does not need oxygen supply cylinders which have to be replaced at intervals.

With a device according to claim 15, the production of oxygen enriched air can be done at times when the bed is not in use so that the sleep of the user is not disturbed by the noise generated by the compressor.

With a device according to claim 16, oxygen is only supplied when the user desires it.

With a device according to claim 17 the supply of oxygen enriched air in the supply cylinder can be kept at a high level at any time, and the periods when the supply cylinder is topped up can be preset by the user.

With a device according to claim 19, other additives and/or fragrances can also be supplied to the space lying between the cover and the surface of the mattress in addition to the oxygen.

With a device according to claim 20, the supply of the treatment gas does not cause any cooling of the surface of the skin.

The further embodiment of the invention according to claim 21 is of advantage with respect to the economical use of the treatment gas.

The further embodiment of the invention according to claim 22 makes it possible to produce the treatment gas centrally for a number of places of use, e.g. in the cellar of a hotel. In view of the fact that the treatment gas is bottled in supply cylinders which are then connected to the conducting device at the place of use, there is no need for any additional line installations in the building.

The further embodiment of the invention according to claim 23 is advantageous with respect to the small size of the supply cylinders. The treatment gas for one night can be stored in small five liter cylinders which can stand unobtrusively in the room.

The invention is described below in greater detail with the aid of design examples and by reference to the attached drawings. In these:

Figure 1:
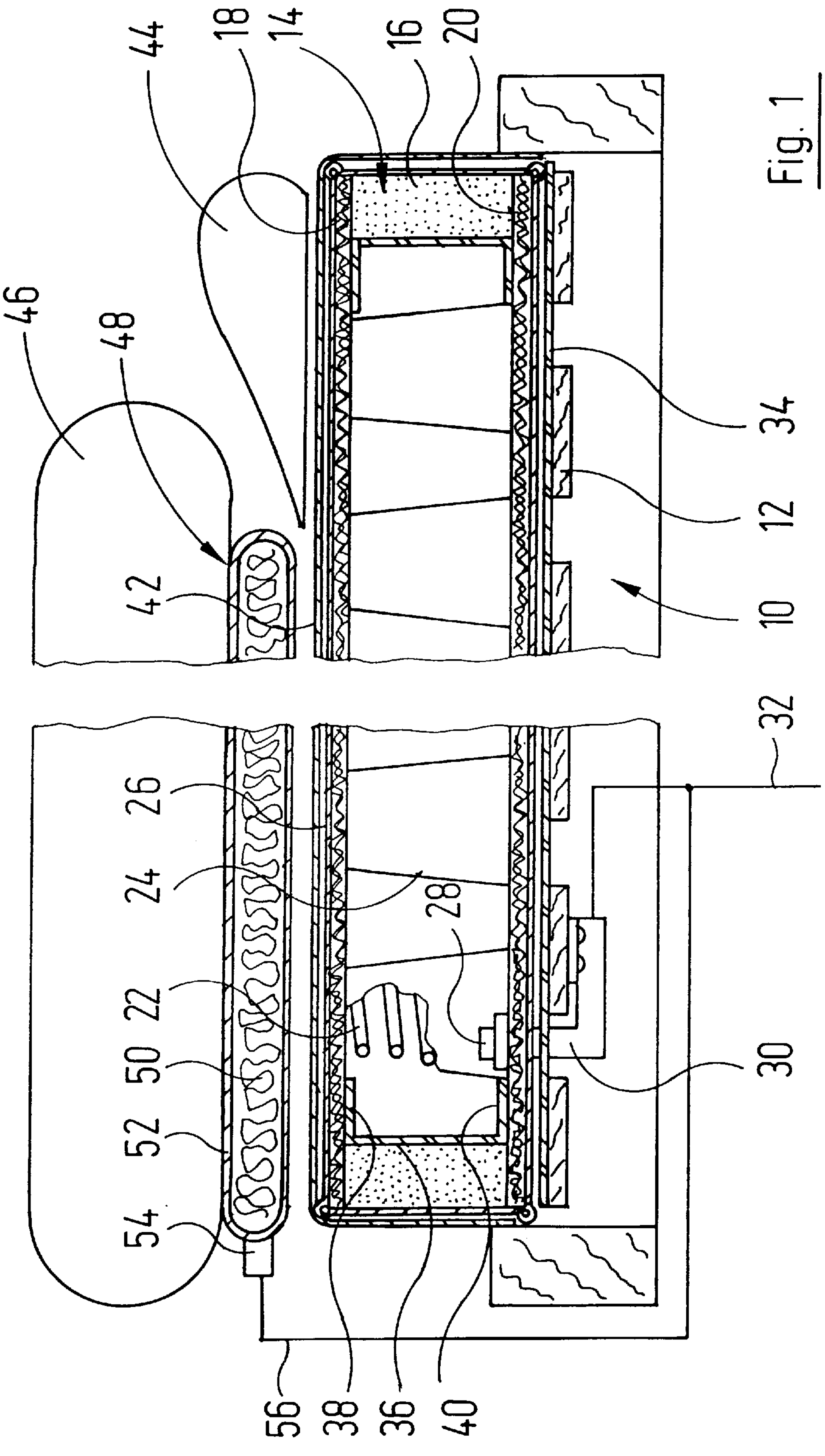
FIG. 1 shows a longitudinal section through a bed which is also used for oxygen therapy.

In FIG. 1 a bed with a slatted frame is designated with the number 10 which supports a modified interior sprung mattress designated by the number 14 on top of slats 12.

The interior spring mattress 14 has a rectangular frame 16 enclosing it which is made of a relatively hard foam material and two cover layers 18, 20 which are made up of fibre mats. There are arranged between the two cover layers 18, 20 springs 22, each of which are sewn into a pocket 24. The complete assembly as described above is sewn into a cover 26. In this respect the construction of the interior sprung mattress 14 is no different from the conventional construction, but it goes without saying that the two cover layers 18, 20 can have different design details (sides for summer or winter use).

Figure 3:
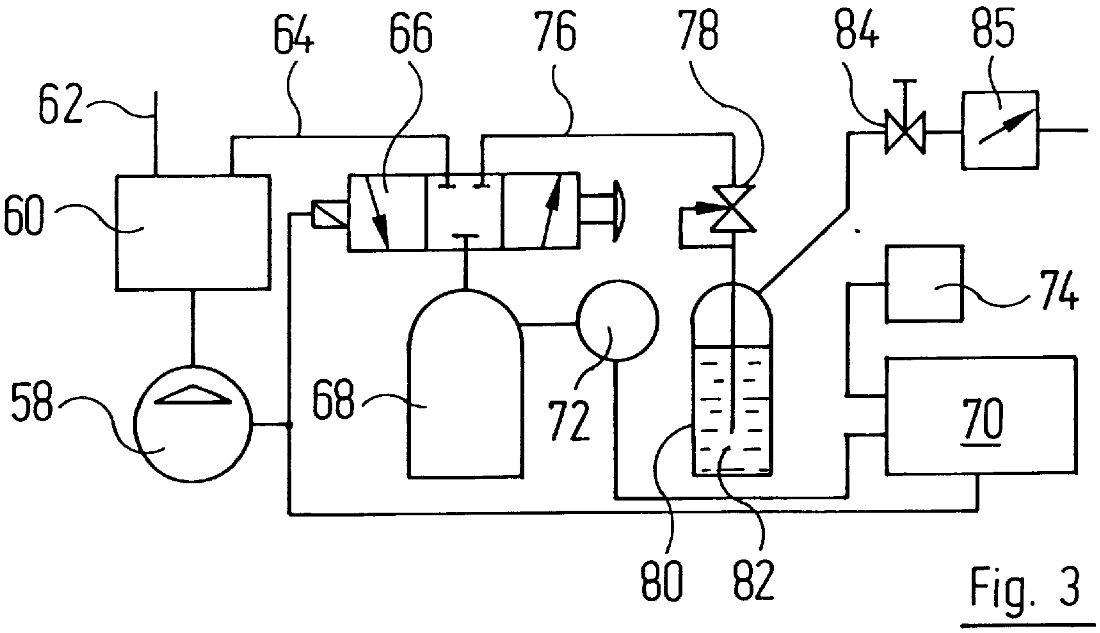
FIG. 3 is a schematic connection diagram of the oxygen supply device for the bed illustrated in FIG. 1.

At the foot area of the interior sprung mattress 14 there is now also fitted into each of the top and bottom surfaces and close to the edge a plug-in connector part 28 which fits together with a plug-in connector part 30 fitted to one of the slats 12 and in this way connects the interior of the interior sprung mattress 14 to a supply line 32, by means of which oxygen enriched air, which can also be mixed with fragrances and/or other additives, is supplied from a supply device which is shown in greater detail in FIG. 3.

In order to prevent any escape of this treatment air through whichever cover layer is bottom-most, there is inserted between the bottom of the interior sprung mattress 14 and the top of the slats 12 a barrier film which is a part of the bed which is separate from the interior sprung mattress 14 and remains in place on the slatted base 10 when the interior sprung mattress 14 is removed. For this purpose, the barrier film 34 can be joined to the upper surfaces of the slats 12 for example by means of self-adhesive strips on its underside.

If the frame 16 for the interior sprung mattress 14 is not naturally already essentially air-impermeable then its inner surface must be covered with an additional barrier film 36. This may also be stretched with edge segments 38. 40 over those marginal areas of the air-permeable cover layers 18, 20 on which a user does not normally lie. The edge segments 38, 40 are therefore broad in the area where the legs lie, narrow in the back area and broad again in the head area. Looking in plan view, the shape of the free edges of the edge segments 38, 40 can, for example, follow the boundary contour of a person lying in the middle of the bed at a distance of approximately 20 to 30 cm.

A sheet 42 is shown laid over the interior sprung mattress 14 which is tucked between the mattress and the slatted base 10 in the standard fashion.

A pillow 44 and also a duvet 46 are shown schematically laid over the interior sprung mattress 14.

An interposed mat designated with the number 48 is shown in the space between the duvet 46 and the top side of the interior sprung mattress 14. This mat has a soft, loosely packed and light fill 50 which may, for example, take the form of a mat made of woollen fibres. Alternatively the fill 50 can take the form of a two-dimensional bead chain made of styropor beads or similar and the individual beads are held by threads passing through them in a flat, lattice-like geometry as will be explained in greater detail later on by reference to FIG. 5.

The fill 50 is encompassed by a permeable cover 52. The latter has a connection piece 54 which is connected to the supply line 32 by means of a connection hose 56.

Lengthwise and widthwise, the interposed mat 48 is somewhat smaller than the duvet 46 so that the edge sections of the duvet 46 which hang down over it also cover the interposed mat 48 and provide a seal against the environment when a person sleeping in the bed lies between the top side of the interior sprung mattress 14 and the underside of the interposed mat 48. If the supply line 32 is supplied with oxygen rich air whilst the user is asleep then this reaches the lowermost parts of the skin through the permeable top side of the interior sprung mattress 14 and the permeable sheet 42 and the also permeable night clothes of the user. Similarly, the oxygen enriched air released by the interposed mat 48 reaches the uppermost parts of the skin.

As a modification to the embodiment shown in FIG. 1, a cover and the interposed mat 48 can also be sewn together. This can then also be placed in a common cover.

If the user does not want to use a duvet, in summer for example, an interposed mat can be used with a cover which does not allow any air to permeate on the top side and in this way takes on the sealing function otherwise provided by the duvet.

The supply of oxygen to the supply line 32 can in principle take place by means of an oxygen cylinder which is changed at intervals and a reducing valve. FIG. 3 shows an oxygen supply device in which oxygen is produced locally.

A compressor 58 supplies an oxygen enriching unit 60 with compressed air. The latter consists of, for example, a membrane which has a different permeability for oxygen and nitrogen. The oxygen enriching unit 60 therefore splits the compressed air supplied into two partial circuits, one of which is a nitrogen rich partial circuit which is discharged via a line 62 and which for preference passes through the wall of the building into the open air. The oxygen rich partial circuit is compressed by means of a line 64 and a 3/3 control valve 66 into a supply cylinder 68 whereby the movement of the control valve 66 into the appropriate operating position is carried out by a control unit 70 adjoined to the compressor 58 simultaneously with the compressor 58 being switched on.

The control unit 70 is supplied with the electric output signal from a pressure transducer 72 which is connected to the interior of the supply cylinder 68 and generates an output signal whenever the pressure inside this cylinder drops below a pre-set value. The control unit 70 receives a second input signal from a switch clock 74, on which the user can set the compressor operating times at which he will not be disturbed by any operation of the compressor 58. The control unit 70 processes the two input signals essentially in AND logic operation.

In a second (embodiment)* of the control valve 66 which is manually adjustable, the interior of the supply cylinder 68 is connected to a mixer cylinder 80 by means of a line 76 and a pressure reducer 78. This cylinder holds a volume of fluid 82 which contains a fragrance and/or an additive. By bubbling the oxygen enriched air through the volume of fluid 82 the fragrance and/or other additive are mixed with the oxygen enriched air. The air so obtained is fed to the supply line 32 by means of a manually operated tap 84.

Translator's note: I think a word has been left out of the text. The literal translation is "in a second of the control valve 66".

A heating unit 85 is shown schematically behind the tap 84 which heats the oxygen enriched air to a temperature which is close to the surface temperature of the skin and which can be adjusted by the user.

Figure 2:
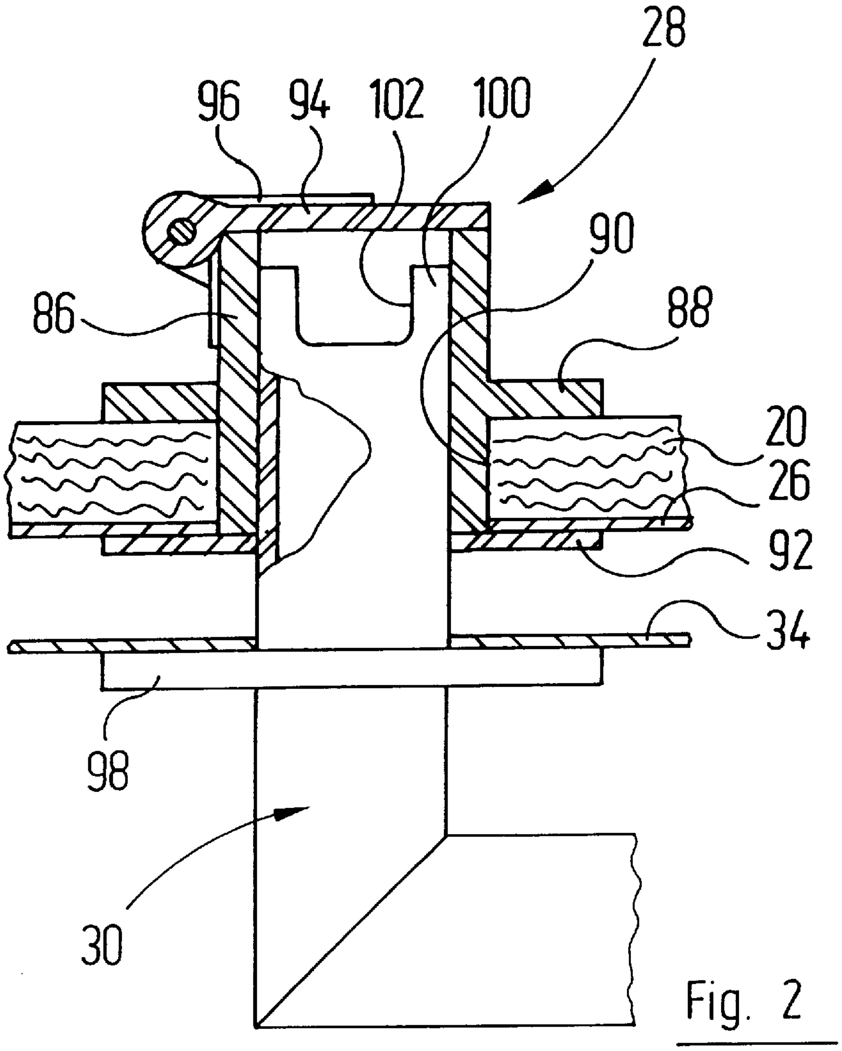
FIG. 2 shows a section through a plug-in connection, by means of which the mattress of the bed shown in FIG. 1 is connected to an oxygen supply line.

As can be seen from FIG. 2, the plug-in connector part 28 has a sleeve section 86 which carries a flange section 88.

The part of the sleeve section 86 below the flange section 88 has an opening 90 going through it, for which allowance is made in the cover layer 20 and the cover 26. A cover disc 92 is glued to the lower face of the sleeve section 86, as a result of which the plug-in connector part 28 is able to pass through the cover layer 20 and the cover 26 and essentially provides a seal for the circulating medium.

The top end of the sleeve section 86 is normally connected by means of a tiltable valve flap 94 which is pre-tensioned into the closing position by means of a wire strap spring 96.

The plug-in connector part 30 carries a limiting flange 98, the position of which is selected so that when it is positioned against the cover disk 92 an upper end section 100 of the plug-in connector part 30 projects over the top end of the sleeve section 86, as a result of which the valve flap 94 is forced to open against the force of the wire strap spring 96. In order to facilitate the admission of the oxygen enriched air into the interior of the interior sprung mattress 14 under these conditions, recesses 102 are provided at the edge of the end section 100.

Figure 4:
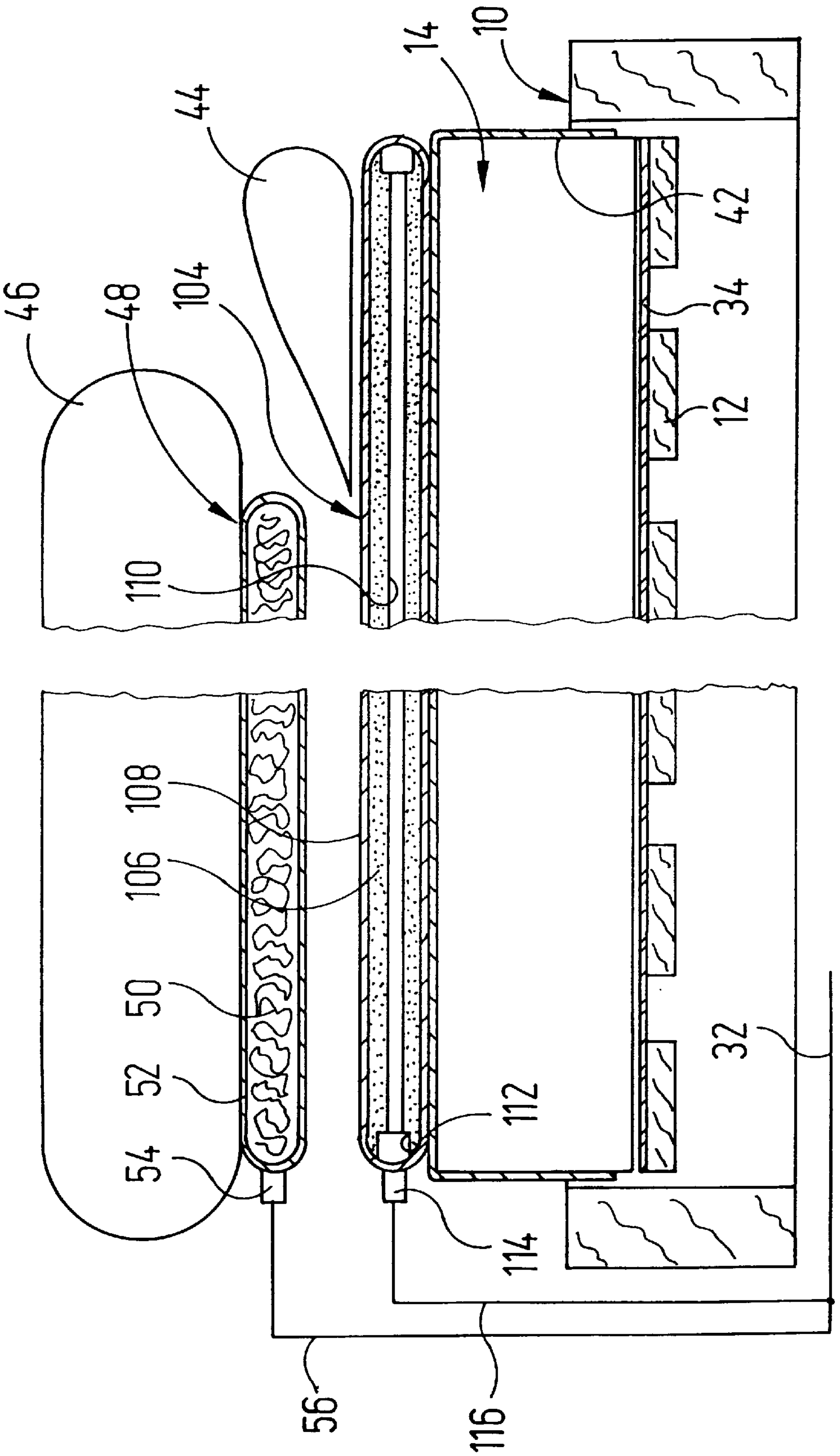
FIG. 4 shows a cross-section through a bed which has been modified for oxygen therapy and which has a conventional mattress.

FIG. 4 shows a modified bed in which a standard mattress is used, the internal construction of which is of no interest here.

A bottom interposed mat 104 is provided over the mattress 14 which once again has an open pore fill 106 and also a cover 108 made of a permeable material. The fill 106 is now however made of hard open pore foam material, the hardness of which may essentially correspond to that of firmer foam interior mattresses. Lengthwise and crosswise running channels 110 are provided in the fill 106 which are connected to a main distribution channel 112 which is fed from a connection piece 114. The latter is in turn connected to the supply line 32 by means of a connection hose 116.

The bottom interposed mat 104 is placed between the top side of the mattress 14 and the sheet 42. In this way the bottom interposed mat 104 ensures the oxygen supply to the lowermost sections of skin of a person lying in bed, in a similar manner to the way in which the modified interior sprung mattress 14 achieves this in the embodiment shown in FIG. 1.

Figure 5:
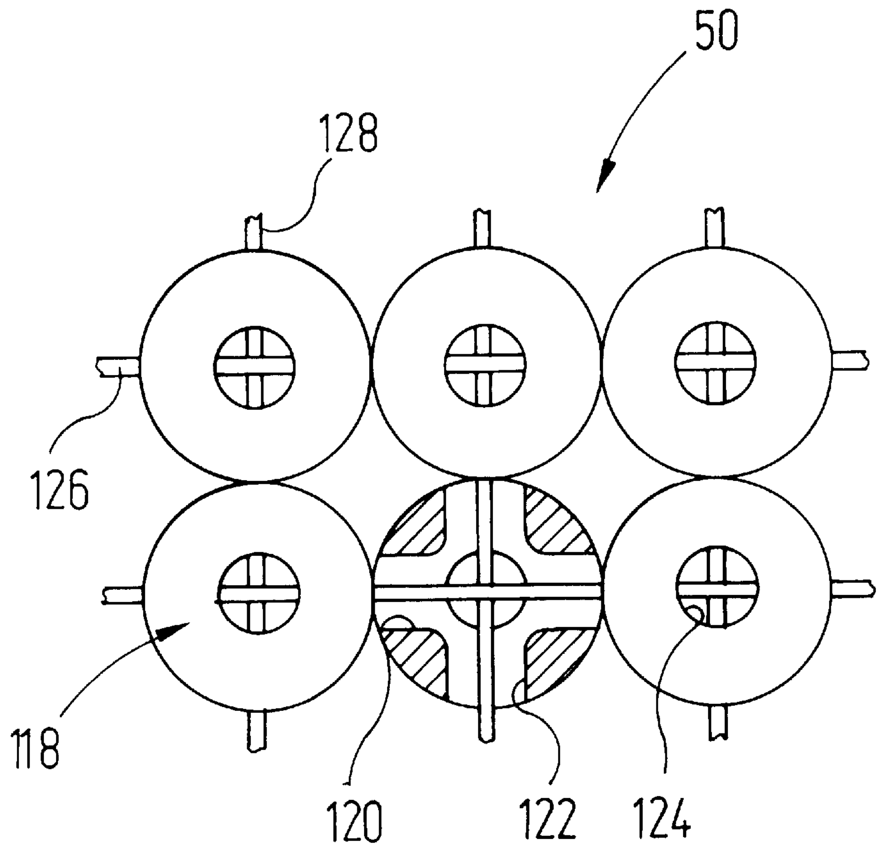
FIG. 5 shows a similar view to FIG. 1 in which a bed is illustrated which has been modified for oxygen therapy.

FIG. 5 shows a cutout from a modified pliable filling material which can be used for the interposed mat 48.

Beads 118 made of styropor or some other light synthetic material have three holes 120, 122, 124 which are perpendicular to each other. Crosswise holding threads 126 and lengthwise holding threads 128 are drawn through the holes 120 and 122 in the surface of the mat. As can be seen, the diameter of the holes 120, 122 and 124 is appreciably larger than the diameter of the holding threads, so that these channels can also be used as passageways for the treatment air. Other passageways, via which the treatment air is distributed over the interposed mat 48, exist between the outer surfaces of the beads 118 and the cover 52, the sides of which are separated by the bead mat.

As an option, a bead mat can be constructed from fibre balls through which the holding threads are drawn using a needle.

Figure 6:
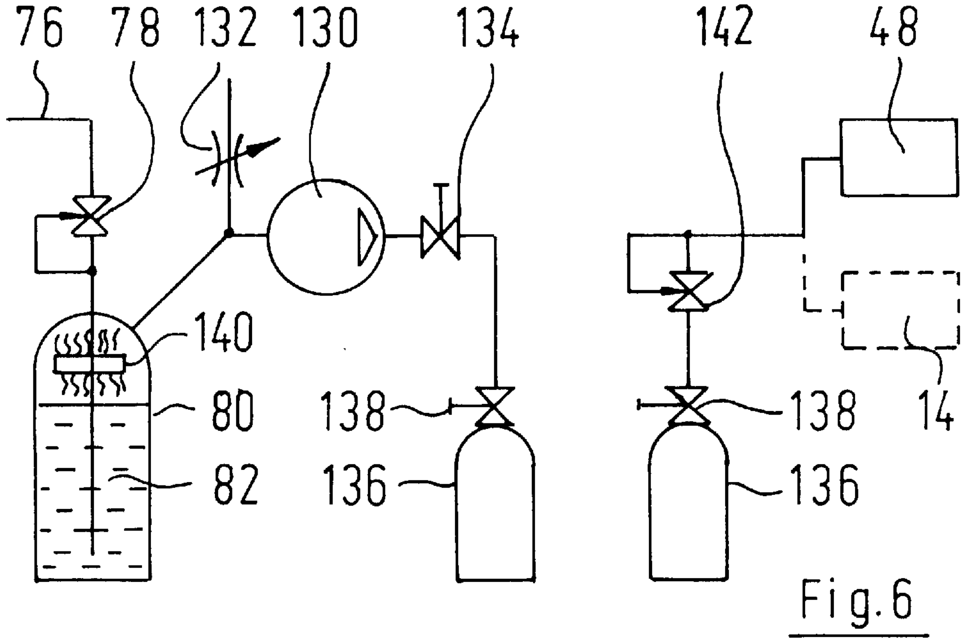
FIG. 6 is a schematic showing the production of treatment gas in a building with a number of places of use, e.g. a hotel.

FIG. 6 shows the production of oxygen enriched air for a number of places of use, e.g. the beds in a hotel or in a clinic.

The production of the treatment gas is in principle carried out in the same way as shown in FIG. 3.

The outlet on the mixer cylinder 80 is now, however, connected to the inlet of another compressor 130. The compressor 130 further draws in ambient air by means of an adjustable throttle 132. The throttle 132 is adjusted so that the total oxygen content of the mix is approximately 38%. This is advantageous in respect of fire protection. The output of the compressor 130 is connected by means of a valve 134 to a supply cylinder 136 which also has a valve 138.

For preference, the fluid volume 82 contains sea salt as an additive and the production of the aerosol made up of oxygen enriched air and fluid is achieved for preference under the simultaneous effect of UV light which is generated by a UV radiator 140 which is positioned in the mixer cylinder (or irradiates into a mixer cylinder which has a quartz window or some other UV permeable window).

After filling the supply cylinders 136, these can then be connected to any bed in the building, the simplest being to connect it only to the interposed mat 48 but if required also to the modified interior sprung mattress 14. The volume of treatment gas supplied can be adjusted by adjusting a pressure reducer 142.

The volume of the supply cylinder 136 is calculated so that the quantity of treatment gas contained in it is sufficient for one night. In practice 5 liter supply cylinders are sufficient for this and are easy to handle. When the supply cylinder 136 is empty, it is routinely replaced when the room is being made up and, for example, the towels are being changed.

The method of supplying a number of places of use with treatment gas as shown in FIG. 6 is simple and low-cost to install without necessitating any building alterations. The part shown in the left of FIG. 6 for the production and compression of the treatment gas can be installed in one of the engineering rooms of the building as a ready pre-installed unit. It essentially only needs an electric socket. The interposed mats 48 are reasonably priced parts which can be installed even in conventional beds without expense.

This gives rise to the possibility of being able to provide oxygen therapy in any available bed as required and at a reasonable cost.

What is claimed is:

1. A device for supplying a person with additional oxygen for cutaneous respiration, comprising a mattress (14) having a head section, a body section, a top side, a lower side and a circumferential portion, the top and lower side being arranged in spaced parallel relationship, a source for treatment gas, the treatment gas being selected from the group consisting of oxygen and oxygen enriched air, distributions means (14; 48; 104) for uniformly supplying the treatment gas to a selected part of a person being treated, the distribution means (14; 48; 104) carrying the treatment gas into a space between the top and lower sides of the mattress, the top and lower sides of the mattress being permeable for gas, and a barrier layer (34) distinct from the mattress (14) covering the lower side of the mattress.

2. The device according to claim 1, wherein the circumferential portion of the mattress comprises a circumferential frame that forms a gas barrier.

3. Device according to claim 1, characterised in that the fill (50) is a loose fibre mat which for preference consists of natural fibres.

4. Device according to claim 1, characterised in that the fill (50) has the form of a number of balls or spherical bodies (118) which for preference are held by threads (126, 128) in a flat lattice-like structure.

5. Device according to claim 1, characterized in that the fill (106) has the form of an open pore foam material which is provided with at least one distribution channel (110) running through the fill (106).

6. Device according to claim 1, characterised in that the mattress is an interior sprung mattress (14).

7. Device according to claim 6, characterised in that the connection (28) is provided on the underside of the mattress (14), preferably in the perimeter area of the foot end section of the mattress.

8. Device according to claim 6, characterised in that the mattress is connected to a supply line (32) for the treatment gas by means of a plug-in connection (28,30).

9. Device according to claim 8, characterised in that there are provided in the top side and underside of the mattress (14), and arranged at geometrically equivalent places, identical, preferably symmetrically eccentric plug-in connector parts (28) each of which has a valve part (94) which is pre-tensioned (96) in the closed position and which is forced to open by means of a plug-in connector part (30) fixed to the base (10) of the bed supporting the mattress when the mattress (14) is laid on it.

10. Device according to claim 1, characterised by a source (58–84) for the treatment gas which consists of a compressor (58) and an oxygen enriching unit (60) which is fed by this, whereby the latter contains a membrane which has a different permeability for oxygen and nitrogen.

11. Device according to claim 10, characterised in that the outlet of the oxygen enriching unit (60) can be connected to a supply cylinder (68) via a control valve (66).

12. Device according to claim 11, characterised in that the supply cylinder (68) is connected to the supply line (32) via a control valve (66) and a pressure reducer (78).

13. Device according to claim 10, characterised by a control unit (70) for the compressor (58) which is supplied with the pressure signal from a pressure transducer (72) connected to the supply cylinder (68) and with the switch signal of a switch clock (74) and sets the compressor (58) in operation when the pressure in the supply cylinder (68) drops below a pre-set level and the present time lies within a switch window set on the switch clock (74).

14. Device according to claim 13, characterised in that the control unit (70), together with the compressor (58) actuates the control valve (66) which is inserted between the compressor and the supply cylinder (68).

15. Device according to claim 10, characterised in that a supply cylinder (136) can be connected to the source for the treatment gas in such a way that it can be detached and to the conducting device (14; 48; 104) for the treatment gas in such a way that it can be detached.

16. Device according to claim 15, characterised in that the source for the treatment gas consists of a compressor (130) which compresses the treatment gas and the supply cylinder (136) is connected to the conducting device (14; 48; 104) via a pressure reducer (142).

17. Device according to claim 1, characterised by a mixer device (80) which also adds at least a fragrance or an additive to the oxygen or the oxygen enriched air.

18. Device according to claim 1, characterised by a heating unit (85) which heats the treatment gas supplied to the conducting device (14; 48; 104).

19. Device according to claim 1, characterized in that the conducting device (14; 48; 104) supplies the treatment gas with preference to areas between the cover (46) and the top surface of the mattress (14) in which a user predominantly lies, whilst the supply of treatment gas to perimeter areas is blocked or reduced.

20. A device for supplying a person with additional oxygen for cutaneous respiration, comprising a mattress (14) having a head section, a body section, a top side, a lower side and a circumferential portion, the top and lower sides being arranged in spaced parallel relationship, a cover (46) overlaying the mattress (14), a source for treatment gas, the treatment gas being selected from the group consisting of oxygen and oxygen enriched air, distribution means (14; 48; 104) for uniformly supplying the treatment gas to a selected part of a person being treated, wherein the distribution means (48) comprises an interposed mat arranged between the cover (46) and the top side of the mattress (14), the interposed mat having a cover (52) which is permeable at least in its underside and which is connected to a source (58–84) of treatment gas.

21. The device in accordance with claim 20, wherein the cover (52) of the interposed mat has walls that are kept apart in spaced relationship by a permeable filling (50) which is provided with at least one distribution channel (110).

22. A device for supplying a person with additional oxygen for cutaneous respiration, comprising a mattress (14) having a head section, a body section, a top side, a lower side and a circumferential portion, the top and lower sides being arranged in spaced parallel relationship, a source for treatment gas, the treatment gas being selected from the group consisting of oxygen and oxygen enriched air, and distribution means (14; 48; 104) for uniformly supplying the treatment gas to a selected part of a person being treated, the distribution means (14; 48; 104) carrying the treatment gas into a space between the top and lower sides of the mattress, at least the top side of the mattress being permeable, the circumferential portion of the mattress comprising a circumferential frame that forms a gas barrier and the mattress being an interior sprung mattress (14).

23. A device for supplying a person with additional oxygen for cutaneous respiration, comprising a mattress (14) having a head section, a body section, a top side, a lower side and a circumferential portion, the top and lower sides being arranged in spaced parallel relationship, a cover (46) overlaying the body section of the mattress (14) and co-operating therewith to define a body-receiving space, and a source for treatment gas, the treatment gas being selected from the group consisting of oxygen and oxygen enriched air, and distribution means (14; 48; 104) for uniformly supplying the treatment gas to the body-receiving space, wherein the circumferential portion of the mattress (14) comprises a circumferential frame that forms a gas barrier, and the distribution means (14; 48; 104) comprises a permeable surface region of the top side of the mattress having a shape substantially conforming to a boundary contour of a person lying on a middle portion of the mattress.

24. The device in accordance with claim 23, wherein the top side of the mattress is gas permeable and said permeable surface region is defined by a barrier layer arranged on the top side and having a cut-out corresponding to the boundary contour.

25. A device for supplying a person with additional oxygen, comprising a source for treatment gas, the treatment gas being selected from the group consisting of oxygen and oxygen enriched air, a conducting device to supply the treatment gas to a selected part of a person being treated, and a mattress of a bed with a top side, a lower side and a circumferential portion, the top and lower sides being arranged in spaced parallel relationship, distribution means (14; 48; 104) carrying the treatment gas into a space between the top and lower sides of the mattress, wherein at least the top side of the mattress is permeable and the circumferential portion of the mattress comprises a circumferential frame that forms a gas barrier, wherein the mattress is an interior sprung mattress (14) connected to a supply line (32) for the treatment gas by a plug-in connection (28; 30), and wherein in the top side and underside of the mattress (14) there are provided and arranged at geometrically equivalent places identical plug-in connector parts (28) each of which has a valve part (94) which is biased (96) into a closed position and which is forced to open by a plug-in connector part (30) fixed to a base (10) of a bedstead supporting the mattress when the mattress (14) is laid thereonto.

26. The device in accordance with claim 25, wherein the plug-in connector parts are symmetrically eccentric.

* * * * *